United States Patent [19]

Mirviss et al.

[11] 4,185,053

[45] Jan. 22, 1980

[54] PROCESS FOR MANUFACTURING SUBSTANTIALLY PURE DIALKYL PHOSPHOROCHLORIDOTHIONATE

[75] Inventors: Stanley B. Mirviss, Stamford, Conn.; Thomas M. Von Lehman, Hartsdale, N.Y.

[73] Assignee: Stauffer Chemical Company, Westport, Conn.

[21] Appl. No.: 838,685

[22] Filed: Oct. 3, 1977

[51] Int. Cl.$^2$ ................................................ C07F 9/20
[52] U.S. Cl. .................................................... 260/986
[58] Field of Search ......................................... 260/986

[56] References Cited

U.S. PATENT DOCUMENTS

| 2,482,063 | 9/1949 | Hechenbleikner | 260/986 |
| 2,692,893 | 10/1954 | Hechenbleikner | 260/986 |
| 2,715,136 | 8/1955 | Toy et al. | 260/986 |
| 2,900,406 | 9/1959 | Vogel et al. | 260/972 |
| 3,089,890 | 5/1963 | Chupp et al. | 260/990 |
| 3,098,866 | 7/1963 | Divine | 260/990 |
| 3,356,774 | 12/1967 | Niermann et al. | 260/981 |
| 3,502,750 | 3/1970 | Anglaret et al. | 260/986 |
| 3,794,703 | 2/1974 | Beck et al. | 260/990 |
| 3,897,523 | 7/1975 | Sorstokke | 260/986 |

FOREIGN PATENT DOCUMENTS

| 1801432 | 4/1973 | Fed. Rep. of Germany | 260/986 |
| 646188 | 11/1950 | United Kingdom | 260/986 |
| 1289396 | 9/1972 | United Kingdom | 260/986 |

*Primary Examiner*—Anton H. Sutto
*Attorney, Agent, or Firm*—Michael E. Zall

[57] ABSTRACT

A process for producing in high yields a substantially pure dialkyl phosphorochloridothionates. The process comprises chlorinating bis(phosphorothioic) sulfides, thioic acids, or salts thereof, distilling the reaction mixtures, contacting the distillate with a thioic acid or salt thereof, contacting the mixture with water and distilling the organic material after the water contacting.

27 Claims, No Drawings

PROCESS FOR MANUFACTURING SUBSTANTIALLY PURE DIALKYL PHOSPHOROCHLORIDOTHIONATE

BACKGROUND OF THE INVENTION

This invention relates to a process for producing in high yields substantially pure phosphorochloridothionate (hereinafter "thionate").

The thionates produced by the process of this invention have the general formula:

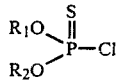
(1)

wherein $R_1$ and $R_2$ are each alkyl substituents of 1 to 12 carbon atoms. The thionates are valuable intermediates in the manufacture of pesticidal agents, flotation agents, plasticizers, lubricating oil additives, rubber curing compounds, flame retardants and many other useful chemicals.

Various processes have been utilized for the production and purification of the aforementioned thionates for example:
(1) U.S. Pat. No. 3,897,523 to Sorstokke;
(2) U.S. Pat. No. 3,794,703 to Beck et al;
(3) U.S. Pat. No. 3,502,750 to Anglaret;
(4) U.S. Pat. No. 3,356,774 to Niermann et al;
(5) U.S. Pat. No. 3,098,866 to Divine;
(6) U.S. Pat. No. 3,089,800 to Chupp et al;
(7) U.S. Pat. No. 2,900,406 to Vogel et al;
(8) U.S. Pat. No. 2,715,136 to Toy et al;
(9) U.S. Pat. No. 2,692,893 to Hechenbleikner;
(10) U.S. Pat. No. 2,482,063 to Hechenbleikner;
(11) British Pat. No. 646,188 to Hechenbleikner;
(12) British Pat. No. 1,289,396 to Hercules, Inc.; and
(13) German Pat. No. 1,801,432 to Knapsack, AG.

The entire disclosures of all of the aforementioned references are incorporated herein by reference.

Generally, commercial quantities of thionates are obtained by chlorinating an initial reactant composition with a chlorinating agent, the reactant composition containing at least one compound which is either:

(1) A bis(phosphorothioic) sulfide of the general formula:

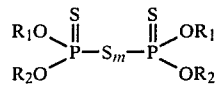
(2)

wherein m is a whole number, preferably 2; or (2) a thioic acid or salt thereof having the general formula:

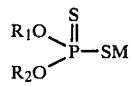
(3)

wherein M is hydrogen, ammonium, an alkaline earth metal or an alkali metal. The chlorinating step produces a crude thionate reaction mixture which contains the thionate and impurities. The crude reaction mixture is usually purified.

The chlorinating agents which can be employed include chlorine, sulfur dichloride, sulfur monochloride, sulfuryl chloride and phosphorus pentachloride.

A process for producing a thionate by chlorinating a bis(phosphorothioic) sulfide is more fully described in, for example, the aforementioned U.S. Pat. No. 2,482,063 to Hechenbleikner.

A process for producing a thionate by chlorinating a thioic acid or salt thereof is more fully described in, for example, the aforementioned U.S. Pat. No. 2,692,893 and British Pat. No. 646,188 to Hechenbleikner.

As indicated the aforementioned processes produce by-product impurities. Illustrative of some of the processes employed to produce thionates and the by-product impurities produced therefrom are the following, wherein M is as previously defined and wherein X is the grouping

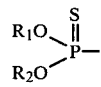

|  | Reactant | Chlorinating Agent | Thionate | By-Product Impurities |
|---|---|---|---|---|
| (a) | 2 XSM | + 3 Cl$_2$ | → 2 XCl | + 2 MCl + S$_2$Cl$_2$ |
| (b) | 2 XSM | + 2 Cl$_2$ | → 2 XCl | + 2 MCl + 2 S |
| (c) | 2 XSM | + 2 S$_2$Cl$_2$ | → 2 XCl | + 2 MCl + 6 S |
| (d) | 2 XSM | + 2 SCl$_2$ | → 2 XCl | + 2 MCl + 2 S |
| (e) | 2 XSM | + 6 SCl$_2$ | → 2 XCl | + 2 MCl + 4 S$_2$Cl$_2$ |
| (f) | 2 XSM | + 2 SO$_2$Cl$_2$ | → 2 XCl | + 2 MCl+2S+2 SO$_2$ |
| (g) | 2 XSM | + Cl$_2$ | → | (X)$_2$S$_2$ + 2 MCl |
| (h) | 2 XSM | + S$_2$Cl$_2$ | → | (X)$_2$S$_4$ + 2 MCl |
| (i) | 2 XSM | + 2 Cl$_2$ | → | (X)$_2$S$_2$ + 2 MCl+S$_2$Cl$_2$ |
| (j) | 2 XSM | + SO$_2$Cl$_2$ | → | (X)$_2$S$_2$ + 2 MCl + SO$_2$ |
| (k) | (X)$_2$S$_2$ | + 2 Cl$_2$ | → 2 XCl | + S$_2$Cl$_2$ |
| (l) | (X)$_2$S$_2$ | + Cl$_2$ | → 2 XCl | + 2S |
| (m) | (X)$_2$S$_2$ | + S$_2$Cl$_2$ | → 2 XCl | + 4S |
| (n) | (X)$_2$S$_2$ | + 4SCl$_2$ | → 2 XCl | + 3 S$_2$Cl$_2$ |
| (o) | (X)$_2$S$_2$ | + SO$_2$Cl$_2$ | → 2 XCl | + 2S |
| (p) | (X)$_2$S$_2$ | + 2SO$_2$Cl$_2$ | → 2 XCl | + S$_2$Cl$_2$ + 2 SO$_2$ |
| (q) | (X)$_2$S$_3$ | + S$_2$Cl$_2$ | → 2 XCl | + 5S |
| (r) | (X)$_2$S$_4$ | + S$_2$Cl$_2$ | → 2 XCl | + 6S |

For example, in a typical type (k) reaction bis(O,O-diethyl phosphorothioic) disulfide is reacted with chlorine to produce O,O-diethyl chlorothiophosphate as follows:

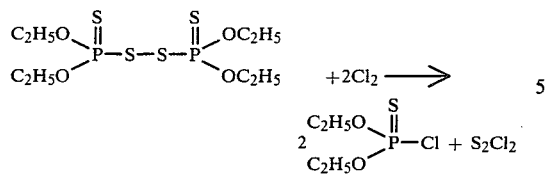

This reaction produces sulfur monochloride as a by-product impurity.

In a typical type (a) reaction O,O-diethyl dithiophosphoric acid is reacted with chlorine to produce O,O-diethyl chlorothiophosphate as follows:

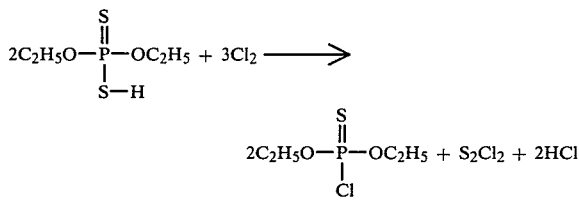

This reaction produces sulfur monochloride and hydrogen chloride as by-product impurities.

Additional impurities may, for example be introduced if the thionate is produced in a two step process. A typical two step process involves treating alcohol with a phosphorus sulfur compound to produce a crude thioic acid composition:

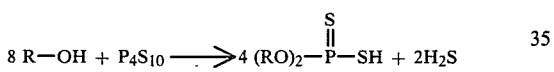

wherein, for example, R is an alkyl substituent having from 1 to 12 carbon atoms. The crude thioic acid reaction mixture is difficult to purify. It is generally used as the initial reactant composition which is directly chlorinated to produce a crude thionate reaction mixture. The crude thionate reaction mixture produced from this two step process, not only has the by-product impurities produced from the chlorination step, but additionally may have contained therein hydrogen sulfide, unreacted alcohol, or the chlorinated products thereof.

Thus, as can be seen from the foregoing, the crude thionate reaction mixture may have contained therein various quantities of by-product impurities such as MCl, $S_2Cl_2$, S, $SO_2$,$(X)_2S_2$,$H_2S$ unreacted alcohol, the chlorinated products of $H_2S$ and unreacted alcohol, unreacted XSM and unreacted chlorinating agent from which the thionate must be separated. A substantial portion of the impurities in the crude thionate reaction mixture is usually sulfur monochloride.

In addition, there are a variety of side reaction impurities which are formed to varying extents depending upon the reaction conditions and the reactants, i.e. the type and amount of chlorinating agent as well as the purity of the bis(phosphorothioic) sulfide or thioic acid or salt thereof subjected to chlorination, which further contaminate the crude thionate reaction mixture.

For example, the crude thionate reaction mixture may be additionally contaminated with side reaction impurities some of which satisfy the structure

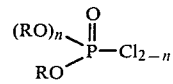

wherein n is 0 or 1, and R is $R_1$ or $R_2$. For example, these side reaction impurities may include one or more compounds having the groups

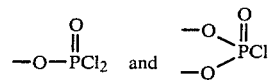

wherein the unsatisfied valences are satisfied by $R_1$ and/or $R_2$.

The need for improving the quality of the crude thionate reaction mixture is readily apparent in subsequent processes employing the same and in the products derived therefrom. Unless a substantially pure thionate is employed, the efficiency of processes employed in preparing derivatives is substantially lowered. For example, the impurity

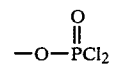

(wherein the unsatisfied valence is satisfied by $R_1$ or $R_2$), which may be obtained in substantial amounts from the chlorination process, contains twice as many reactive groups (i.e. chlorine substituents) as the desired thionate. Additionally, this impurity contains the

which reacts to products which do not have the desirable properties of the corresponding thionate derivatives.

Many attempts have been made to remove the impurities from crude thionate reaction mixture in order to produce a purer thionate product, for example:

SOLVENT EXTRACTION TREATMENT

Extraction of the crude thionate reaction mixture with an organic solvent has been utilized to remove impurities. This method is not satisfactory from a commercial standpoint due to the similar solubility characteristics of the thionate and the associated impurities. Satisfactory separation of the desired thionate product from the impurities by this technique requires several extractions which result in losses of the thionate.

WATER CONTACTING/HYDROLYSIS

Separation of sulfur monochloride, from a crude thionate reaction mixture or a distilled crude thionate reaction mixture, can be accomplished by water hydrolysis. Water hydrolysis can be performed by slowly admixing the crude thionate reaction mixture with water. The sulfur monochloride is hydrolyzed to water soluble acids, i.e. hydrochloric and thiosulfurous, and other products.

Hydrolysis of the sulfur monochloride in the thionate reaction mixture, however produces free sulfur. The sulfur may take a number of forms including crystals, colloidal particles, or syrupy, plastic semi-solids. Particularly in commercial operations, such material causes considerable difficulty in the separation and recovery of the organic layer containing the thionate.

Additionally, water contacting/hydrolysis treatment does not substantially remove all impurities, including all of the sulfur monochloride.

DISTILLATION

Removal of impurities, including non-sulfur containing phosphorus compounds, has been attempted by fractional distillation.

The method is not satisfactory from a commercial standpoint due to the close proximity of the boiling points of the impurities and the thionate.

A satisfactory separation of the thionate from the impurities by distillation is not possible unless repeated several times. Thionate yields may be reduced by reaction of sulfur monochloride with the thionate at high distillation temperatures. Additionally, at elevated temperatures other side reactions can occur which cause the formation of sulfur which can cause fouling of the distillation apparatus.

THIOIC ACID TREATMENT

Another method for purifying crude thionate reaction mixtures is admixing and reacting a dialkyl phosphorodithioic acid with the crude thionate reaction mixture to react with some of the impurities to form additional thionate. The method is not completely satisfactory since the reaction mixture contains a substantial amount of impurities which do not react with the thioic acid. Additionally, the yield of thionate based on the total quantity of thioic acid used is low because the thioic acid which is not converted to thionate is not recovered. This method of treatment is described in detail in the aforementioned Beck reference.

None of the aforementioned methods for treating a crude thionate reaction mixture or known combinations thereof have been wholly satisfactory in producing high yields of substantially pure thionate.

It is therefore an object of the present invention to provide a method for the production in high yields of a substantially pure thionate.

Further objects and advantages inherent in the present invention will become apparent to those skilled in the art from the following disclosure.

BRIEF DESCRIPTION OF THE INVENTION

The present invention is a process for producing dialkyl phosphorochloridothionate compounds of the formula:

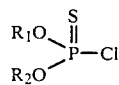

wherein $R_1$ and $R_2$ are each alkyl substituents of 1 to 12 carbon atoms.

The process is comprised of the following process steps:

(a) chlorinating with a chlorinating agent an initial reactant composition containing at least one compound selected from the group consisting of:

(i) a bis(phosphorothioic) sulfide of the formula:

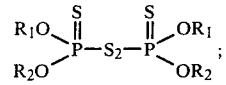

and (ii) a first thioic acid or salt thereof of the formula:

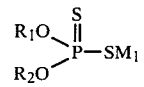

wherein $M_1$ is selected from the group consisting of hydrogen, ammonium, an alkaline earth metal and an alkali metal, to produce a crude thionate reaction mixture containing the thionate and a quantity of impurities;

(b) distilling the crude thionate reaction mixture to produce an initial thionate distillate containing the thionate and a lesser quantity of impurities.

(c) admixing and reacting with the initial thionate distillate a second thioic acid or salt thereof of the general formula:

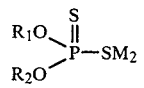

wherein $M_2$ is selected from the group consisting of hydrogen, ammonium, alkaline earth and an alkali metal, to react with at least some of the impurities to produce a semi-pure thionate reaction mixture;

(d) contacting the semi-pure thionate reaction mixture with water to produce an organic phase and a water phase; and (e) distilling the organic phase to produce a final distillate of substantially pure thionate and a residue fraction.

Unexpectedly, there is substantially, no sulfur precipitation during the contacting step (d).

Preferably, the process further comprises recycling the residue fraction for use as all or part of the initial reactant composition and repeating at least steps (a) and (b), i.e. chlorinating the initial reactant composition and distilling the crude thionate reaction mixture produce therefrom.

It is particularly preferred that the process further comprise recycling the residue fraction for use as all or part of the initial reactant composition and repeating process steps (a) through (e) to produce a final thionate distillate of substantially pure thionate in high yields.

It is particularly preferred that the process be carried out in a continuous manner.

DETAILED DESCRIPTION OF THE INVENTION

By the use of the term "yields" or "percent yield" it is meant the fraction or percent which the actual quantity of thionate produced is to the theoretical quantity of thionate that would be produced if all of the bis(phosphorothioic) sulfide or first thioic acid and second thioic acid were converted to thionate.

The term "alkyl substituent", means a monovalent radical derived from a branched or straight chain saturated hydrocarbon by removal of one hydrogen atom and having the general formula $C_nH_{2n+1}$ wherein n is a whole number.

The term "ammonium", means the monovalent radical —NH4.

The term "alkaline earth metal" means the elements magnesium, calcium, strontium, barium and radium.

The term "alkali metal" means the elements lithium, sodium, potassium, rubidium, cesium and francium. Particularly preferred alkali metals are sodium and potassium.

As indicated previously, the chlorinating agents can be chlorine, sulfur dichloride, sulfur monochloride, sulfuryl chloride and phosphorus pentachloride. A particularly preferred chlorinating agent is chlorine.

Preferably $R_1$ and $R_2$ are the same alkyl substituents. It is particularly preferred that $R_1$ and $R_2$ be the same alkyl substituents, each being an alkyl substituent of 1 to 8 carbon atoms.

It is preferred that the thioic acid or salt thereof be the same as the second thioic acid or salt thereof, and particularly preferred that $M_1$ and $M_2$ both be hydrogen, i.e. the first thioic acid is the same as the second thioic acid.

It is also preferred that the mole ratio of the quantity of the second thioic acid or salt thereof to the quantity of impurity in the initial thionate distillate is at least about 0.5:1, and preferably no greater than about 2:1. A mole ratio of about 1:1 is particularly preferred.

It has been found that at mole ratios of less than about 0.5:1 sulfur precipitation begins to occur during the contacting step (d).

A mole ratio of greater than about 2:1 becomes economically impractical and unnecessary, although the invention is operative.

Sulfur monochloride as indicated previously is a substantial portion of the total impurities in the crude thionate reaction mixture and is carried over to the initial thionate distillate; therefore the ratio of the quantity of the second thioic acid or salt thereof to the quantity of sulfur monochloride impurity in the initial thionate distillate should preferably be at least about 0.5:1 and preferably no greater than about 2:1. A mole ratio of about 1:1 is particularly preferred.

A particularly preferred embodiment of the process of this invention is a process for producing in high yields a substantially pure thionate compound of the general formula:

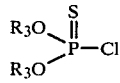

wherein $R_3$ is an alkyl substituent of 1 to 8 carbon atoms. The process is comprised of the following process steps:

(a) chlorinating with chlorine an initial reactant composition containing at least one compound selected from the group consisting of:

(i) a bis(phosphorothioic) sulfide of the formula:

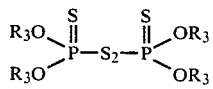

and (ii) a thioic acid of the general formula:

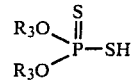

to produce a crude thionate reaction mixture containing the thionate and sulfur monochloride;

(b) distilling the crude thionate reaction mixture to produce an initial thionate distillate containing the thionate and sulfur monochloride;

(c) admixing and reacting with the initial thionate distillate a quantity of the thioic acid sufficient to react with at least some of the sulfur monochloride to produce a semi-pure thionate reaction mixture;

(d) contacting the semi-pure thionate reaction mixture with water to produce an organic phase and a water phase;

(e) distilling the organic phase to produce a final thionate distillate of substantially pure thionate and a residue fraction;

(f) recycling the residue fraction for use as the initial reactant composition and repeating at least steps (a) and (b).

Again, it is particularly preferred that the process further comprise of repeating process steps (c) through (e) to produce a final thionate distillate of substantially pure thionate at high yields.

It is also particularly preferred that the process be a continuous process.

It is preferred that the mole ratio of the quantity of thioic acid admixed and reacted with the initial thionate distillate to the quantity of sulfur monochloride contained therein be at least about 0.5:1 and preferably no greater than about 2:1. A mole ratio of about 1:1 is particularly preferred.

The process of this invention is particularly suited for producing in high yields, substantially pure dimethyl and diethyl phosphorochloridothionate.

More specifically, chlorinating the initial reactant composition is accomplished by known methods in the art, for example as described in the aforementioned Hechenbleikner references.

Suitable inert organic solvents may be employed in the process. Such solvents include carbon tetrachloride, chloroform, benzene, toluene, xylene, chlorobenzene, tetrachlorethane, methylene chloride, ethylene dichloride and the like. It is preferred however that no solvent be used during the chlorination.

The chlorination is preferably carried out at a temperature within the range of from about 0° to 80° C. However, temperatures outside this range may be employed depending upon the type of reactants utilized. Cooling means may be necessary, since the reaction is somewhat exothermic, particularly in the early stages.

It has unexpectedly been found that lower chlorination temperatures may be utilized, i.e. about 40° C. and below, without causing sulfur precipitation during the contacting step (d) while still maintaining high yields of substantially pure thionate product.

Distillation of the crude thionate reaction mixture step (b)) and the organic phase (step (e)) are accomplished by known methods in the art. The distillation is generally carried out under reduced pressure.

Distillation of the crude thionate reaction mixture substantially separates the impurities from the crude thionate reaction mixture to produce an initial thionate distillate containing the thionate and a lesser quantity of impurities. As indicated previously, a substantial portion of the impurities in the initial thionate distillate is sulfur monochloride. The residue from the distillation consists of higher boiling impurities.

Distillation of the organic phase, produced by contacting the semi-pure thionate reaction mixture with water, separates impurities and water from the thionate to produce a final thionate distillate of substantially pure thionate. The residue fraction containing higher boiling impurities can be recycled to the chlorination step (a). A substantial portion of the residue fraction will be the bis(phosphorothioic) sulfide of formula (2).

More particularly, the crude thionate reaction mixture or the organic phase is subjected to distillation to remove low boiling materials which are characteristic of the particular chlorinating reaction (step (a)) or admixing and reacting (step (c)), i.e. hydrogen chloride, hydrogen sulfide, sulfur dioxide, alkyl chlorides, inert organic solvents, and the like, which boil below the boiling point of the desired thionate. Subsequently, the thionate distillate is produced by distilling the remainder under reduced pressure.

Distillation may be accomplished by a wiped film evaporator, wherein a vaporous fraction containing the thionate is formed and separated from a residue fraction containing relatively non-volatile material. The vaporous fraction is emitted from the evaporator to a condenser. The residue is discharged from the evaporator as a liquid.

The residue from distilling step (b) and residue fraction from distilling step (e) may be trasnferred to, for example, a by-product recovery system where the residue material may be converted to useful products such as phosphoric acid and sulfur.

Optionally, the residue fraction from distilling step (e) may be recycled to be utilized as the initial reactant composition for chlorinating wherein the bis(phosphorothioic) sulfide and/or thioic acid is converted to thionate.

Distillation of the crude thionate reaction mixture produces an initial thionate distillate which is then admixed and reacted with a thioic acid or salt thereof (step (c)).

The process step of admixing and reacting the initial thionate distillate with a quantity of a thioic acid or salt thereof is preferably accomplished by adding the thioic acid or salt thereof to the initial thionate distillate and mixing for a period of at least one minute at a temperature of about 10° C. to about 80° C.

It is essential that the alkyl substituents of the second thioic acid or salt thereof correpond to the alkyl substituents of the thionate being produced. Thus, for example, if the process is being utilized to produce dimethyl phosphorochloridothionate, dimethyl phosphorodithioic acid or its salt thereof is utilized. Likewise, if the process is being utilized to produce diethyl phosphorochloridothionate, diethyl phosphorodithioic acid or its salts thereof is utilized.

A sufficient quantity of thioic acid or salt thereof is added to react with at least some of the impurities in the initial thionate distillate to produce a semi-pure thionate reaction mixture.

Unexpectedly, it has been found that upon subsequently contacting the semi-pure thionate reaction mixture with water, the sulfur precipitate which usually accompanies such contacting is eliminated.

Generally, the second thioic acid or salt thereof may be added to the initial thionate distillate in a quantity such that the mole ratio of the second thioic acid or salt thereof to the quantity of impurities in the initial thionate distillate is at least about 0.5:1 and preferably no greater than about 2:1. It is particularly preferred that the mole ratio be about 1:1.

The quantity and type of impurities in the initial thionate distillate can be readily determined by methods well known in the art, i.e. KI method for determining sulfur monochloride (see, for example, "Studies in the Chemical Behavior of Some Compounds of Sulfur", Proceedings of the Indian Academy of Science, 1953, Pages 17–22).

It has been found that sulfur monochloride is the predominant impurity contained in the initial thionate distillate. The quantity of sulfur monochloride may be used to determine the quantity of second thioic acid or salt thereof required. The mole ratio of the thioic acid or salt thereof to the sulfur monochloride in the initial thionate distillate should be at least about 0.5:1 and preferably no greater than 2:1. It is particularly preferred that the mole ratio be 1:1.

Generally, the length of time for which the thioic acid or salt thereof is admixed with the initial thionate distillate depends upon various factors, i.e. batch size, mixing procedure, impurities, temperature and the like.

It has been found however, that a period of about 1 minute to about 1 hour is sufficient for the thioic acid or salt thereof to react with at least some of the impurities.

The addition of the thioic acid or salt thereof to the initial thionate distillate may be accomplished at from about 10° C. to about 80° C. It is preferred however that the temperature be from about 20° C. to about 45° C.

The admixing and reacting of the thioic acid or salt thereof with the initial thionate distillate produces a semi-pure thionate reaction mixture which is then contacted with water [step (d)].

The step of contacting the semi-pure thionate reaction mixture with water is both a hydrolysis process and a liquid-liquid extraction process.

The contacting step comprises contacting the semi-pure thionate reaction mixture with water and thereafter separating the organic and aqueous phases. The temperature of contacting with water can vary widely, e.g. 5° C. to 75° C., but is preferably conducted in the range of from about 10° C. to about 50° C. The time of contacting and the amount of water utilized can also vary depending upon the amount of impurities, the improvement in quality or up-grading desired, the available equipment, the rate and type of contacting (e.g., simple shaking, bubbling water up through the composition, counter-current or concurrent flow, mechanical agitation, the temperature of contacting, and the like). In other words, the time or duration of contact between the water and the semi-pure thionate reaction mixture and the amount of water utilized will be dictated by the designs of the manufacturer. In general, the time for contacting should be as short as required to achieve the desired degree of upgrading. In general, the amount of water utilized will be in the range of 0.1 to 10 volumes of water for each volume of semi-pure thionate reaction mixture. In a one-stage contact operation about 0.25 to about 2.5 volumes of water for each volume of semi-pure thionate reaction mixture constitute a satisfactory ratio.

The water in which some of the impurities are soluble forms an aqueous phase and the thionate is contained in an organic phase. The two phases are separated and the water phase transferred to, for example, a by-product recovery system. The organic phase is then distilled [step (e)].

The distilling of the organic phase is, as previously described, accomplished by methods well known in the art.

In order to produce substantially pure thionate in high yields it is particularly preferred that the residue fraction from the distilling step (e) be recycled for use as the initial reactant composition in the chlorinating step and subsequently performing at least the step of distilling. Preferably the distillate from this distilling step is subjected to the admixing and reacting step, the contacting step and the distilling step.

The initial reactant composition used in the chlorinating step may not only consist of the recycled residue fraction from step (e) but may consist of an additional makeup quantity of bis(phosphorothioic) sulfide or thioic acid or salt thereof.

In a continuous type operation the residue fraction from distilling step (e) may be continuously recycled for use as the initial reactant composition and a makeup quantity of bis(phosphorothioic) sulfide or thioic acid or salt thereof continuously added thereto.

As indicated previously, it has unexpectedly been found that the addition of the second thioic acid or salt thereof to the initial thionate distillate not only increases the final yield of thionate when the residue fraction is recycled, but also eliminates the sulfur precipitate which usually accompanies the water contacting/hydrolysis treatment.

Further, the process of this invention is an improvement over the prior art processes in that the whole or a part of the chlorination step can be completed at lower temperatures, i.e., 40° C. and below without sulfur precipitation in the contacting step (d), decreased purities or decreased yields. Lower temperatures favor the formation of sulfur monochloride, and reduced sulfur precipitation during chlorination, but do not favor the formation of other by-product impurites.

Chlorinating at low temperatures (thus producing increased quantities of sulfur monochloride) in combination with only thioic acid treatment would necessitate the use of large quantities of thioic acid to react with the sulfur monochloride. Such large quantities of thioic acid would be essentially wasted without a method of recycling the reacted or unreacted thioic acid.

Chlorinating at low temperatures in combination with only the water contacting/hydrolysis treatment would result in the precipitation of copious quantities of sulfur due to the reaction of the sulfur monochloride with water.

Surprisingly and unexpectedly admixing and reacting the thioic acid or salt thereof with the initial thionate distillate results in the conversion of the sulfur monochloride impurity to a bis(phosphorothioic) sulfide which does not cause precipitation of sulfur upon contacting with water and can be recycled for chlorination to the desired thionate.

Thus, as can be seen from the foregoing, the process of this invention is particularly advantageous over prior art processes in that thionate yields and purity are increased under more favorable process reaction conditions.

The following are non-limiting examples of the process of this invention which will give a more complete understanding of the invention and its advantages.

EXAMPLE 1

Dimethyl Phosphorochloridothionate

A 500 ml flask was charged with 158 grams (1 mole) of dimethyl phosphorodithioic acid. The thioic acid was heated to 60° C. and 77 grams (1.08 mole) of chlorine were bubbled into the mixture for a period of two hours to produce a crude thionate reaction mixture.

The crude thionate reaction mixture was distilled in a wiped film evaporator at a skin temperature of 90°–95° C. under 5 mm vacuum. The initial thionate distillate produced (135.7 grams) was analyzed, by the KI titration method, and found to contain 6.9% by weight sulfur monochloride (0.070 moles).

To a stirred solution of 134 grams of the initial thionate distillate, 13.0 grams of dimethyl phosphorodithioic acid (0.082 moles) were added slowly, while maintaining the temperature below 45° C.

The resultant semi-pure thionate reaction mixture was stirred for 15 minutes, then added slowly with agitation to 105 ml. distilled water. The organic layer was separated and redistilled to produce a final thionate distillate. The distillate, 102.1 grams, was analyzed and found to be more than 99% dimethyl phosphorochloridothionate. The residue fraction, 19.5 grams was a brown oil.

A 500 ml flask was then charged with 158 grams (1 mole) of dimethyl phosphorodithioic acid and 16.2 grams of the brown residue fraction. While this solution was stirred at 60° C. to 65° C., 81.3 grams (1.14 moles) of chlorine was bubbled into the mixture for a period of 2 hours to produce a crude thionate reaction mixture. Distillation of this crude thionate reaction mixture yielded 144 grams of an initial thionate distillate containing 6.0% $S_2Cl_2$ (0.064 moles). To 141.5 grams of this distillate was added 12.0 grams (0.76 moles) of dimethyl phosphorodithioic acid. The resultant mixture was hydrolyzed with 120 grams of water and redistilled. The final thionate distillate 113.0 grams was analyzed and found to be more than 99% dimethyl phosphorochloridothionate. The residue, 16.7 grams was retained for further recycling.

EXAMPLE 2

Diethyl Phosphorochloridothionate

A 500 ml flask was charged with 186 grams (1 mole) of diethyl phosphorodithioic acid. The thioic acid was heated to 60° C. and 77 grams (1.08 mole) chlorine was bubbled into the mixture for a period of two hours to produce a crude thionate reaction mixture.

The crude thionate reaction mixture was distilled as in Example 1 yielding 161.6 grams of an initial thionate distillate containing impure diethyl phosphorochloridothionate. The distillate contained 2.2% $S_2Cl_2$ (0.026 moles). To a stirring solution of 159 grams of the distillate at ambient temperature was added 9.5 grams of diethyl phosphorodithioic acid (0.051 moles). The resultant mixture was added slowly to 126 grams of water. After separation of the two phases, the organic phase was distilled yielding 138.0 grams of greater than 99% pure diethyl phosphorochloridothionate. The residue fraction was 13.1 grams of a brown oil.

Another 186 grams of diethyl phosphorodithioic acid was added to 11.4 grams of the residue fraction and the mixture was chlorinated as above, with 81 grams of chlorine (1.14 moles). Distillation yielded 170.8 grams of an initial thionate distillate The initial thionate distillate contained 2.1% $S_2Cl_2$ (0.027 moles). Addition of 9.9 grams of diethyl phosphorodithioic acid (0.053 moles) followed by water washing and distillation resulted in 145.5 grams of greater than 99% pure diethyl phosphorochloridothionate and 13.1 grams of recyclable residue. Overall yield based on chlorinated thioic acid was 74.4%.

EXAMPLE 3

Water Washing or Dimethyl Phosphorochloridothionate (DMPCT)—Sulfur Monochloride Mixtures Three solutions of DMPCT containing 10% by weight $S_2Cl_2$ were prepared. One solution was water washed and redistilled without further treatment. The other two solutions were treated with dimethyl phosphorodithioic acid (DMPTA) as described in Example 1. The results presented in the table below demonstrate the increased DMPCT obtained in the treated samples and the elimination of sulfur precipitate in the water contacting step. There was no recycle of the residue fraction.

TABLE I

| DMPTA ADDITION AND WATER-WASH OF $S_2Cl_2$-DMPCT MIXTURES | | | |
|---|---|---|---|
| | BLANK | RUN 2 | RUN 3 |
| Wt. Ratio DMPCT: $S_2Cl_2$ | 300:33 | 300:33 | 300:33 |
| Wt. of DMPTA Added | NONE | 78 g | 39 g |
| Mole Ratio DMPTA: $S_2Cl_2$ | — | 2:1 | 1:1 |
| Wt. of Sulfur Precipitate | 7.2 g | 0 | 0 |
| Wt. of Final Thionate Distillate | 270 g | 277 g | 278 g |
| Assay Final Thionate Distillate (% of DMPCT) | 99% | 99% | 99% |
| Wt. Residue Fraction | 21 g | 89 g | 57 g |

EXAMPLE 4

Dimethyl Phosphorochloridothionate

A 500 ml flask was charged with 158 grams (1 mole) dimethyl phosphorodithioic acid. The thioic acid was heated to 60° C. and 56 grams (0.788 moles) of chlorine was bubbled into the mixture for a period of 1.5 hours to produce a reaction mixture which was then cooled to 35° C. 26 grams (0.366 moles) of chlorine was additionally bubbled into the mixture for a period of 0.5 hours to produce a crude thionate reaction mixture.

The crude thionate reaction mixture was distilled through a wiped film evaporator at a skin temperture of 90°-95° C. under 5 mm Hg. vacuum. The initial thionate distillate produced was 162.8 grams and was analyzed by KI titration method and found to contain 11.5% by weight sulfur monochloride (0.14 moles).

To a stirring solution of 160 grams of the initial thionate distillate, 25 grams of dimethyl phosphorodithioic acid (0.16 moles) was added slowly, while maintaining the temperature below 45° C.

The resultant semi-pure thionate reaction mixture was stirred for 15 minutes, then added slowly with agitation to 150 ml distilled water. The organic layer was separated and distilled to produce a final thionate distillate. This distillate, 114.1 grams was analyzed and found to contain greater than 99% dimethyl phosphorochloridothionate. The residue fraction, 41.8 grams was a brown oil.

A 500 ml flask was then charged with 158 grams (1 mole) of thioic acid and 38 grams of the brown residue fraction. While this solution was stirred at 60° C. to 65° C., 58 grams (0.816 moles) of chlorine was bubbled into the mixture for a period of 1.5 hours to produce a reaction mixture which was then cooled to 35° C. 30.7 grams (0.432 moles) of chlorine was additionally bubbled into the mixture for a period of 0.5 hours to produce a crude thionate reaction mixture. Distillation of this crude thionate reaction mixture yielded 179.5 grams of an initial thionate containing 11.6% $S_2Cl_2$ (0.16 moles). To 178 grams of this distillate was added 29 grams (0.18 moles) of dimethyl phosphorodithioic acid. The resultant mixture was hydrolyzed with 150 grams of water and distilled. The final thionate distillate, 121 grams, was analyzed and found to contain greater than 99% dimethyl phosphorochloridothionate. The residue, 53.8 grams was retained for further recycling.

What is claimed is:

1. A process for producing dialkyl phosphorochloridothionate compounds of the formula:

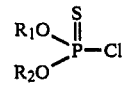

wherein $R_1$ and $R_2$ are each alkyl substituents of 1 to 12 carbon atoms, which comprises:
 (a) chlorinating with a chlorinating agent an initial reactant composition containing at least one compound selected from the group consisting of:
  (i) a bis(phosphorothioic) sulfide of the formula:

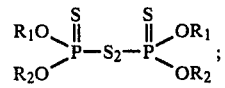

and
  (ii) a first thioic acid or salt thereof of the formula:

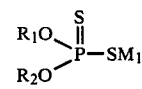

wherein $M_1$, is selected from the group consisting of hydrogen, ammonium, alkaline earth metal and alkali metal, to produce a crude thionate reaction mixture containing the thionate and a quantity of impurities;
 (b) distilling the crude thionate reaction mixture to produce an initial thionate distillate containing the thionate and a lesser quantity of impurities;
 (c) admixing and reacting with the initial thionate distillate a second thioic acid or salt thereof of the formula

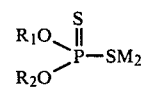

wherein $M_2$ is selected from the group consisting of hydrogen, ammonium, alkaline earth and alkali metal, to react with at least some of the impurities to produce a semi-pure thionate reaction mixture;
 (d) contacting the semi-pure thionate reaction mixture with water to produce an organic phase and a water phase; and (e) distilling the organic phase to produce a final thionate distillate of substantially pure thionate and a residue fraction.

2. The process of claim 1, further comprising recycling the residue fraction for use as the initial reactant composition and repeating at least steps (a) and (b).

3. The process of claim 2, further comprising repeating steps (c) through (e).

4. The process of claim 3, wherein the process is a continuous process.

5. The process of claim 1, wherein $R_1$ and $R_2$ are the same alkyl substituents.

6. The process of claim 1, wherein the first thioic acid or salt thereof is the same as the second thioic acid or salt thereof.

7. The process of claim 6, wherein $M_1$ and $M_2$ are both hydrogen.

8. The process of claim 1, wherein the chlorinating agent is selected from the group consisting of chlorine, sulfur dichloride and sulfur monochloride.

9. The process of claim 1, wherein the chlorinating agent is chlorine.

10. The process of claim 1, wherein the mole ratio of the quantity of the second thioic acid or salt thereof to the quantity of impurity in the initial thionate distillate is at least about 0.5:1.

11. The process of claim 10, wherein the mole ratio is not greater than about 2:1.

12. The process of claim 10, wherein the impurity is sulfur monochloride.

13. The process of claim 11, wherein the impurity is sulfur monochloride.

14. The process of claim 13, wherein the mole ratio is about 1:1.

15. A process for producing in high yields a substantially pure dialkyl phosphorchloridothionate of the formula:

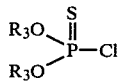

wherein $R_3$ is an alkyl substituent of 1 to 8 carbon atoms which comprise:
(a) chlorinating with chlorine an initial reactant composition containing at least one compound selected from the group consisting of:
(i) a bis(phosphorothioic) sulfide of the formula:

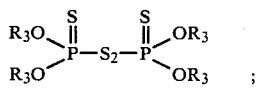

and
(ii) a thioic acid of the general formula:

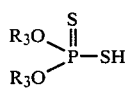

to produce a crude thionate reaction mixture containing the thionate and sulfur monochloride;
(b) distilling the crude thionate reaction mixture to produce an initial thionate distillate containing the thionate and sulfur monochloride;
(c) admixing and reacting with the initial thionate distillate a quantity of the thioic acid to react with at least some of the sulfur monochloride impurity to produce a semi-pure thionate reaction mixture;
(d) contacting the semi-pure thionate reaction mixture with water to produce an organic phase and a water phase;
(e) distilling the organic phase to produce a final thionate distillate of substantially pure thionate and a residue fraction.

16. The process of claim 15, further comprising recycling the residue fraction for use as the initial reactant composition and repeating at least steps (a) and (b).

17. The process of claim 15, further comprising repeating steps (c) through (e).

18. The process of claim 17, wherein the process is a continuous process.

19. The process of claim 17, wherein the mole ratio of the quantity of thioic acid admixed and reacted with the initial thionate distillate to the quantity of sulfur monochloride contained wherein is at least about 0.5:1.

20. The process of claim 19, wherein the mole ratio is not greater than 2:1.

21. The process of claim 19, wherein the mole ratio is about 1:1.

22. The process of claim 17, wherein $R_3$ is an alkyl substituent of 1 to 2 carbon atoms.

23. The process of claim 17, wherein the step of admixing and reacting is accomplished at a temperature of about 10° C. to about 80° C. for a period of from about 1 minute to about 1 hour.

24. The process of claim 23, wherein the temperature is not greater than about 45° C.

25. The process of claim 17, wherein the chlorination step is performed at a temperature not greater than about 40° C.

26. A process for producing in high yields a substantially pure thionate compound of the formula:

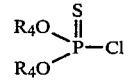

wherein $R_4$ is an alkyl substituent of 1 to 2 carbon atoms, which comprise:
(a) chlorinating with chlorine an initial reactant composition containing at least one compound selected from the group consisting of:
(i) a bis(phosphorothioic) sulfide of the formula:

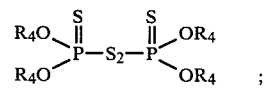

and
(ii) a thioic acid of the formula:

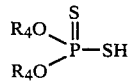

to produce a crude thionate reaction mixture containing the thionate and sulfur monochloride;
(b) distilling the crude thionate reaction mixture to produce an initial thionate distillate containing the thionate and sulfur monochloride;

(c) admixing and reacting with the initial thionate distillate a quantity of the thioic acid sufficient to react with at least some of the sulfur monochloride to produce a semi-pure thionate reaction mixture;

(d) contacting the semi-pure thionate reaction mixture with water to produce an organic phase and a water phase;

(e) distilling the organic phase to produce a final thionate distillate of substantially pure thionate and a residue fraction;

(f) recycling the residue fraction for use in the initial reactant composition and repeating steps (a) through (e).

27. The process of claim 26, wherein the process is a continuous process.

* * * * *